United States Patent
Bish et al.

(12) 
(10) Patent No.: US 11,103,722 B1
(45) Date of Patent: Aug. 31, 2021

(54) LIGHT THERAPY WEARABLE

(71) Applicant: Biothread LLC, Wayne, PA (US)

(72) Inventors: Daniel Bish, New York, NY (US); Lawrence A. Blaustein, Chagrin Falls, OH (US); Jaleh Factor, Manhattan Beach, CA (US); Boris Kontorovich, Brooklyn, NY (US); Daniel Shuter, New York, NY (US); Jay Tapper, Wayne, PA (US); Jeff Michaelson, Huntington Woods, MI (US)

(73) Assignee: BIOTHREAD LLC, Wayne, PA (US)

( * ) Notice: Subject to any disclaimer, the term of this patent is extended or adjusted under 35 U.S.C. 154(b) by 0 days.

(21) Appl. No.: 16/878,071

(22) Filed: May 19, 2020

(51) Int. Cl.
*A61N 5/06* (2006.01)
*A61N 5/067* (2006.01)

(52) U.S. Cl.
CPC ...... *A61N 5/0613* (2013.01); *A61N 2005/063* (2013.01); *A61N 2005/067* (2013.01); *A61N 2005/0645* (2013.01); *A61N 2005/0651* (2013.01)

(58) Field of Classification Search
CPC ............ A61N 5/0613; A61N 2005/063; A61N 2005/0645; A61N 2005/0651; A61N 2005/067

USPC .......................................................... 607/89
See application file for complete search history.

(56) References Cited

U.S. PATENT DOCUMENTS

| 9,687,669 | B2 * | 6/2017 | Stephan | .................. A61F 13/14 |
| 2003/0213044 | A1 | 11/2003 | Wilkinson | |
| 2003/0022468 | A1 | 12/2003 | Koch | |
| 2018/0356579 | A1 | 12/2018 | Holbery | |
| 2019/0083809 | A1 * | 3/2019 | Zhang | .................. A61N 5/0616 |
| 2019/0374792 | A1 * | 12/2019 | Tapper | ................. A61N 5/0622 |

FOREIGN PATENT DOCUMENTS

| CN | 103355769 | 10/2013 |
| WO | 2018118673 | 6/2018 |

* cited by examiner

*Primary Examiner* — Aaron F Roane
(74) *Attorney, Agent, or Firm* — Rankin, Hill & Clark LLP

(57) ABSTRACT

A wearable for providing light therapy to a wearer includes at least one fabric panel having an inner surface that when the wearable is worn is configured to face a wearer's skin and an outer surface opposite the inner surface and at least one side-emitting optical fiber affixed to at least one of the inner surface and the outer surface. The side-emitting optical fiber is optically connectable with an optical fiber light source and configured to project light having a therapeutic wavelength toward a wearer of the wearable. With the fabric panel laid flat, the side-emitting optical fiber includes at least one looped section that bends around more than 180 degrees.

15 Claims, 13 Drawing Sheets

LIGHT THERAPY WEARABLE

BACKGROUND

Clinical studies have demonstrated the ergogenic and prophylactic benefits of red and infrared light therapy. Red and infrared light has been found to increase blood flow to the muscles and joints, which creates an anti-inflammatory response, in addition to providing increased pliability. Muscle and joint stiffness and soreness have been demonstrated to be significantly reduced while muscle contractile function was simultaneously improved by using red and infrared light.

Red and infrared light therapy is utilized by professional athletes, in addition to being widely available in medical spas and physical therapy outlets. Likewise, at the very high end of the consumer market, light therapy awareness and usage has grown.

Building on this awareness, there has also been a plethora of non-light-based wraps and sleeves that have invaded social media, espousing anti-inflammatory and muscle recovery messages. While affordable and accessible, these products only provide temporary relief of symptoms, with little to no recovery or preventative benefits.

Clothing made from light emitting fabrics is described in U.S. Pat. No. 4,234,907. This patent, however, describes such clothing as a fad item or as safety clothing to emit light outward when the wearer wishes to be seen. US 2007/0089800A1 discloses garment systems that include an integrated infrastructure for monitoring vital signs of an individual and for other monitoring purposes. Neither of the aforementioned patent documents discloses a garment for delivering light of a therapeutic wavelength toward a wearer of the garment.

SUMMARY

In view of the foregoing, a wearable for providing light therapy to a wearer includes at least one fabric panel having an inner surface that when the wearable is worn is configured to face a wearer's skin and an outer surface opposite the inner surface and at least one side-emitting optical fiber embroidered to at least one of the inner surface and the outer surface. The side-emitting optical fiber is optically connectable with an optical fiber light source and configured to project light having a therapeutic wavelength toward a wearer of the wearable.

In addition to or alternatively from the wearable described above, a wearable for providing light therapy to a wearer of the wearable can include at least one side-emitting optical fiber affixed to at least one of the inner surface and the outer surface. The at least one side-emitting optical fiber has an allowable bend radius, which is a smallest radius that the at least one side-emitting optical fiber can be bent before damage occurs to the side-emitting optical fiber that impacts its ability to transmit light along the length of the side-emitting optical fiber. Spacing, which is measured perpendicular to the direction in which the at least one side-emitting optical fiber is running, between adjacent sections of the at least one side-emitting optical fiber along at least a portion of the at least one side-emitting optical fiber is less than the allowable bend radius.

In addition to or alternatively from the wearables described herein, each end of the at least one side-emitting optical fiber can be optically connectable with an optical fiber light source and configured to project light having a therapeutic wavelength toward a wearer of the wearable. With the at least one fabric panel laid flat, the at least one side-emitting optical fiber includes at least one looped section that bends around more than 180 degrees.

In addition to or alternatively from the wearables described herein, a wearable for providing light therapy to a wearer of the wearable can include at least one non-optical fiber light source affixed to at least one of the inner surface and the outer surface and positioned on the fabric panel so as to project light toward a wearer of the wearable. The at least one non-optical fiber light source can have a respective side-emitting optical fiber of the at least one side-emitting optical fiber on opposite sides of the at respective non-optical fiber light source.

In addition to or alternatively from the wearables described herein, a wearable for providing light therapy to a wearer of the wearable can include at least one side-emitting optical fiber affixed to at least one of the inner surface and the outer surface, where each end of the at least one side-emitting optical fiber is optically connectable with the at least one optical fiber light source and configured to project light having a therapeutic wavelength toward a wearer of the wearable. When affixed to the at least one fabric panel, the at least one side-emitting optical fiber having a length in meters no less than the quotient of 0.46 and the average attenuation of the at least one side-emitting optical fiber.

DETAILED DESCRIPTION

Figure 1:
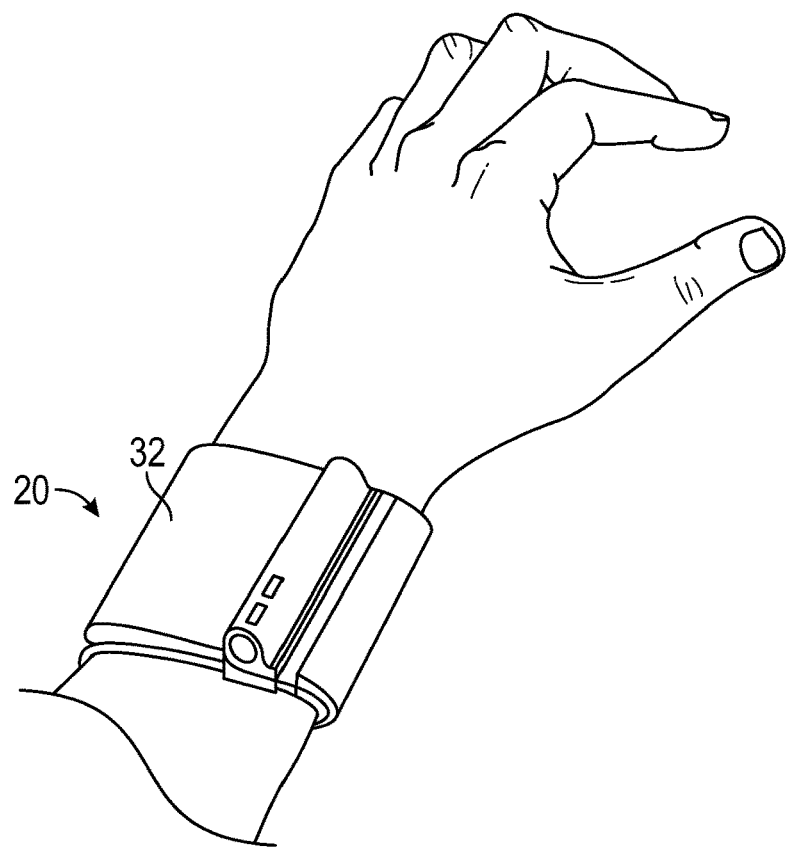
FIG. 1 is a perspective view of a light therapy wearable in the form of a wrap wrapped around a person's wrist.
Figure 2:
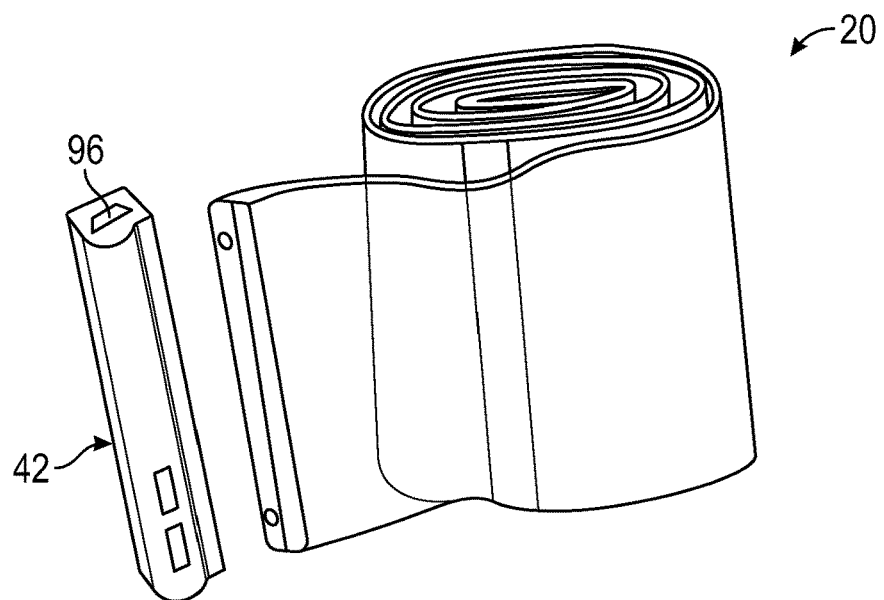
FIG. 2 is a perspective view of the wrap shown in FIG. 1 with an electrical assembly removed from the wrap.

Light having a wavelength between 630 nm and 900 nm has been found beneficial to increase blood flow and may provide ameliorative effects with regard to inflammation, as well as other health benefits. As such, light with this wavelength can be referred to as light having a therapeutic wavelength. FIGS. 1 and 2 depict a light therapy wearable in the form of wrap 20 for providing light therapy to a wearer. The wrap 20 is configured to project light having a therapeutic wavelength toward a person wearing the wrap 20. The wrap 20 can be configured to project light toward targeted body areas, which can include particular muscles, muscle groups, joints, human extremities, and the wearer's skin as examples. The wrap 20 shown in FIGS. 1 and 2 is designed to be worn by a person in a similar manner as a conventional wrap that one may wear around a wrist, arm, ankle, leg, knee, etc.

Figure 3:
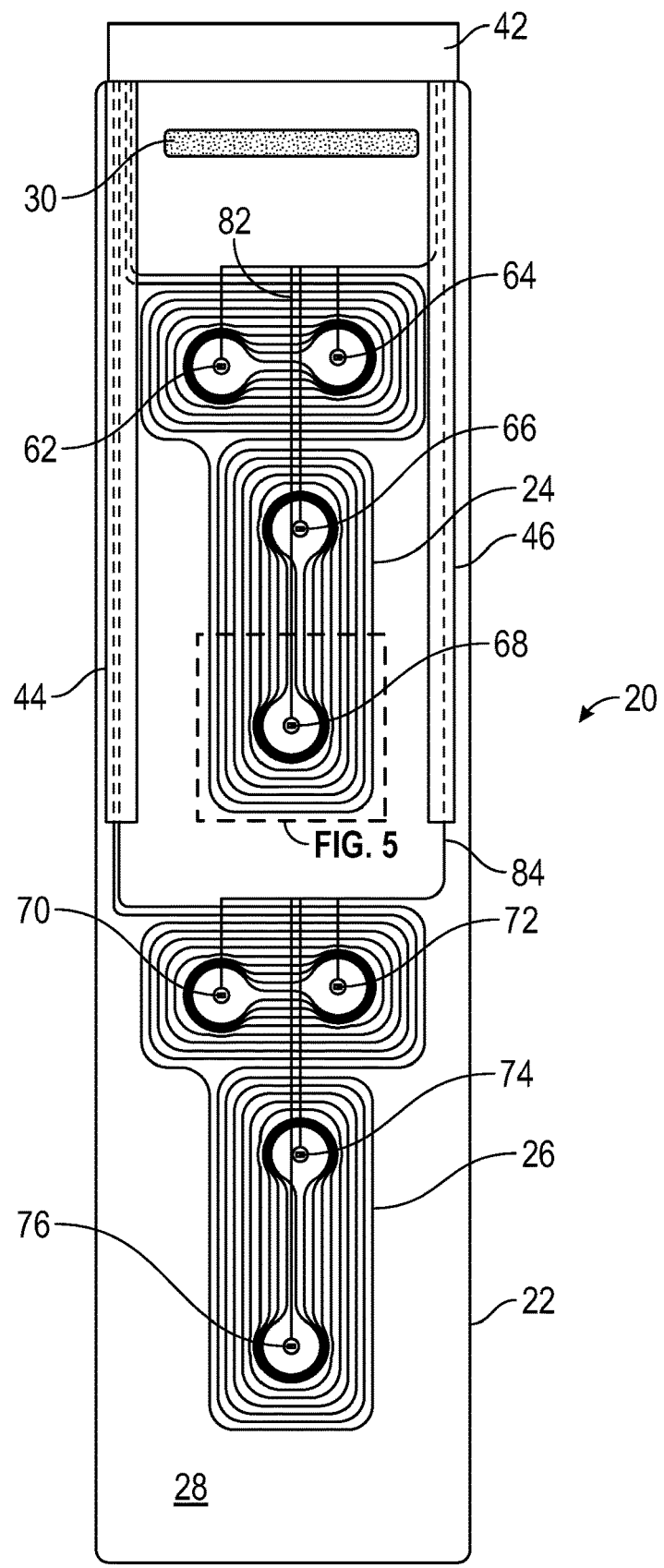
FIG. 3 is a plan view of the wrap of FIG. 1 laid flat showing an inner surface of the wrap.

With reference to FIG. 3, the wrap 20 includes at least one fabric panel 22 and at least one side-emitting optical fiber, which in the illustrated embodiment includes a first side-emitting optical fiber 24 and a second side-emitting optical fiber 26. The side-emitting optical fibers 24, 26 can have a core of high-purity polymethyl methacrylate and cladding of a fluorinated polymer. The side-emitting optical fibers 24, 26 can have an average outer diameter of about 0.25 mm and an average attenuation (at 650 nm) of 0.4 dB/m. Side-emitting optical fibers 24, 26 having other specifications could also be employed. The wrap 20 may include a plurality of fabric panels that are sewn or affixed together in another manner, and the wrap 20 may also include a plurality of side-emitting optical fibers.

FIG. 3 is a plan view showing an inner surface 28 of wrap 20. In FIG. 3, the wrap 20 is laid out on a surface with the inner surface 28 facing up. The wrap 20 includes a closure, e.g. a hook and loop strip 30, that latches to an outer surface 32 when in the orientation shown in FIG. 1. Other types of closures, e.g. snaps and buttons, can be provided. Moreover, the wrap 20 could be sewn together at opposite ends and be pulled over the area in which it is to be worn. When the wrap 20 is worn, the inner surface 28 faces a wearer's skin and the outer surface 32 (see FIG. 1) faces away and is opposite to the inner surface 28. In the illustrated embodiment, the side-emitting optical fibers 24, 26 are affixed to the inner surface 28. Each side-emitting optical fiber 24, 26 is optically connectable with an optical fiber light source 34, 36, 38, 40 (see FIG. 4) located in an electrical assembly 42, which will be described in more detail below. Each optical fiber light source 34, 36, 38, 40 directs light into a respective end 24a, 24b, 26a, 26b of a respective side-emitting optical fiber 24, 26. Light escapes from the outer side of the side-emitting optical fibers 24, 26 along the length of the side-emitting optical fibers 24, 26 so as to provide therapeutic light energy toward the wearer.

The fabric panel 22 can be made from a panel similar to a cut and sew pattern piece or fully fashioned knitted structure. Cut and sew garments are made by using standard fabric, which can come in large rolls, and pattern pieces are cut from the standard fabric and then sewn together using sewing machine. In contrast, fully fashioned knitwear is manufactured using a process of shaping a knitted structure by increasing or decreasing the number of needles or wales where the knitted structure is more engineered so that each knitted structure is made with little or no extra fabric. Where the fabric panel 22 is similar to a cut and sew pattern piece, the fabric panel 22 is shown in FIG. 1 after being cut from a standard fabric roll, for example. Where the fabric panel 22 is fully knitted structure, the fabric panel 22 is shown after manufacturing the knitted structure.

The yarn from which fabric panel 22 is made can provide a comfort component for the wrap 20. Examples of such yarn can include cotton, polyester, cotton/polyester blends, microdenier polyester/cotton blends, and combinations thereof. It can be desirable to provide the wrap 20 so that it is skin-tight or form-fitting to bring the therapeutic light, which is being emitted from each side-emitting optical fiber 24, 26, very close to the wearer of the wrap 20. Accordingly, the yarn can also include an elastic fiber such as lycra or spandex, and more than one type of yarn can form the fabric panel 22.

The fabric panel 22 can be made from fabric having a four way stretch, i.e., the fabric panel 22 can have 100% or nearly 100% recovery along the grain and cross grain from 8% stretch. Alternatively, the fabric panel 22 can be made from fabric having 100% or nearly 100% recovery along the grain and cross grain from 30% stretch. When the fabric panel 22 is similar to a cut and sew pattern pieces, the fabric panel 22 can be either woven or knitted. The side-emitting optical fibers 24, 26 have little or no elasticity. The side-emitting optical fibers 24, 26 typically include glass or plastic covered by a cladding, and the glass or plastic limits the elasticity. For example, the side-emitting optical fibers 24, 26 can have a yield point of 4 N. By providing the fabric panel 22 with the aforementioned stretch and recovery, the fabric panel 22 can provide for a skin-tight form-fitting wrap 20 when the wrap 20 is finally assembled. Since the intensity of light is inversely proportional to the square of the distance from the light source, bringing the side-emitting optical fibers 26, 24 very close to the wearer's skin by providing a form-fitting wrap 20 can increase the efficacy and therapeutic benefit of the wrap 20.

The fabric panel 22 can also be provided with tunnels 44, 46 which can allow for the tunneling of components of the wrap 20. Two tunnels 44, 46 are shown in FIG. 3, however, a fewer or greater number of tunnels can be provided. Each tunnel 44, 46 is a double-layer construction of fabric. Each tunnel 44, 46 could be made with the fabric panel 22, for example, knitted into the knitted structure that makes up a fabric panel 22. Or, each tunnel 44, 46 could be another fabric layer sewn or affixed to the fabric panel 22, for example where the fabric panel 22 is similar to a cut and sew panel.

Unlike being woven or knitted into the fabric panel 22 similar to a typical yarn that makes up the fabric panel 22, the side-emitting optical fibers 24, 26 are affixed to the inner surface 28 or the outer surface 32 of the fabric panel 22 after the fabric panel 22 has been made, e.g., it is an additional step in the manufacturing process. By affixing each side-emitting optical fiber 24, 26 to the inner surface 28 or the outer surface 32 of the fabric panel 22 after the fabric panel 22 has been made, one example of which being through the use of embroidery stitches 48 (FIG. 5), more freedom as to the location and density of the side-emitting optical fiber 24, 26 is available in manufacturing the wrap 20. The side-emitting optical fibers 24, 26, however, can be affixed to the fabric panel 22 in other manners, which will be described in more detail below.

Figure 5:
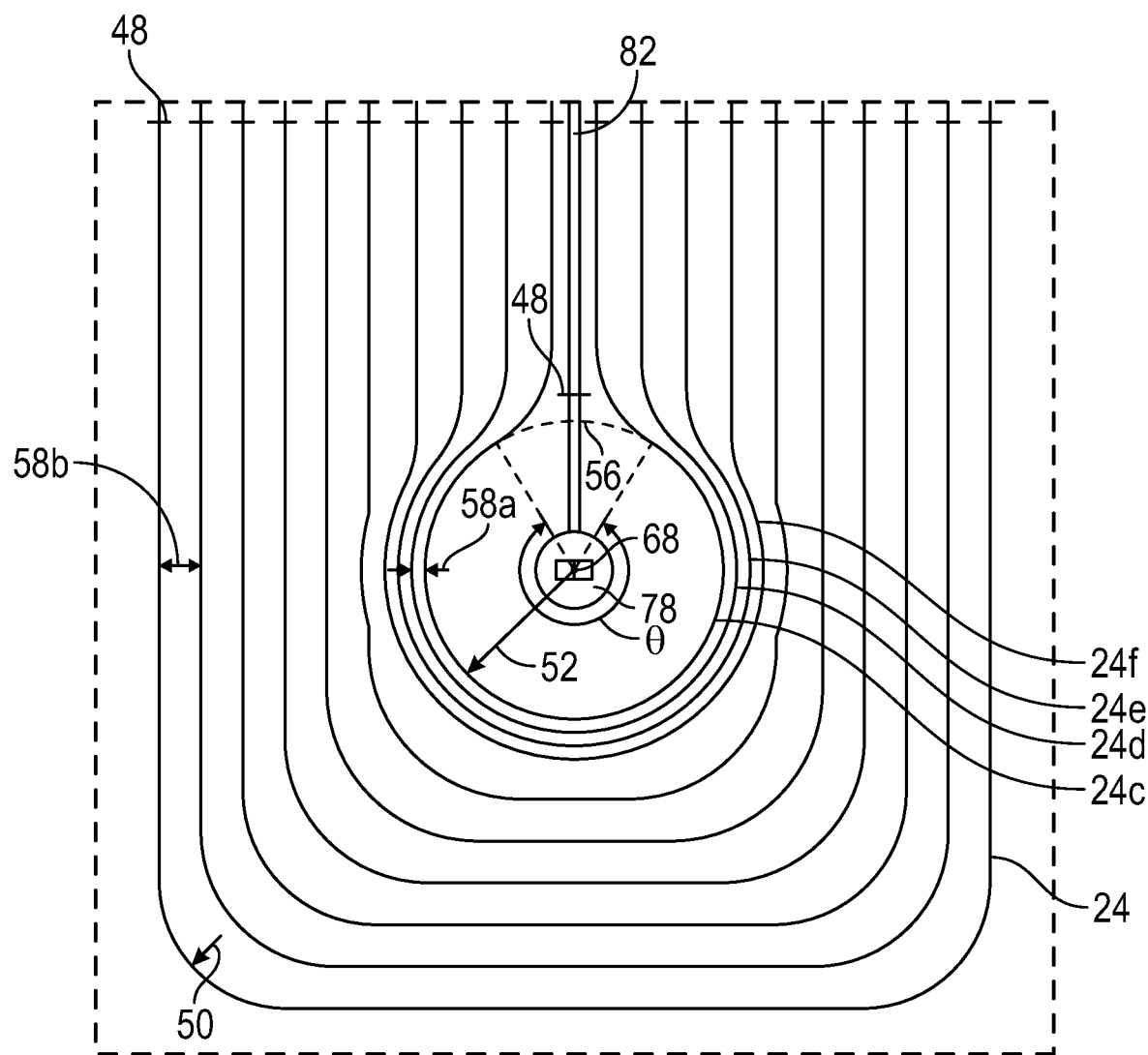
FIG. 5 is a close-up view of a portion of the garment shown in FIG. 3.

FIG. 5 depicts a close-up view of the fabric panel 22 and a portion of the first side-emitting optical fiber 24. The first side-emitting optical fiber 24 is laid out having a pattern with the first side-emitting optical fiber 24 having sections that are bent at different radii. In FIG. 5, bent sections of the first side-emitting optical fiber 24 having a maximum radius 50 and a minimum radius 52 are depicted. Side-emitting optical fibers have an allowable bend radius, which is a property of the side-emitting optical fiber. If the side-emitting optical fiber is bent to a radius smaller than the allowable bend radius, then damage can occur to the side-emitting optical fiber that impacts its ability to transmit light along the length of the side-emitting optical fiber. Known glass optical fibers, for example those used in the telecommunications industry, typically have an allowable bend radius that is at least 20 times the outer diameter of the glass optical fiber. Some known plastic optical fibers have an allowable bend radius that is at least 36 times the outer diameter of the plastic optical fiber.

The first side-emitting optical fiber 24 is laid out such that the minimum radius 52 is greater than or equal to the allowable bend radius. For example, where the first side-emitting optical fiber 24 is a plastic optical fiber having an outer diameter that is 0.250 mm and allowable bend radius that is at least 36 times the outer diameter, the minimum radius 52 is at least 9 mm. To further mitigate against light loss, the minimum radius 52 can be at least 50 times the outer diameter of the side-emitting optical fiber. In the example where the first side-emitting optical fiber 24 is a plastic optical fiber having an outer diameter that is 0.250 mm, the minimum radius can be 12.5 mm.

Spacing, which is measured perpendicular to the direction in which the first side-emitting optical fiber 24 is running, between adjacent sections of the first side-emitting optical fiber 24 along much of the first side-emitting optical fiber 24 is less than the minimum radius 52. Such a lay out allows relatively large length of side-emitting optical fiber to be placed in relatively small area as compared to if the spacing was equal to the allowable bend radius. The layout also allows for good light emission consistency along the length of the side-emitting optical fiber 24. The spacing between adjacent sections of the first side-emitting optical fiber 24, however, need not be equal to one another. For example, for the section of the first side-emitting optical fiber 24 that follows the minimum radius 52, the spacing between adjacent sections of the first side-emitting optical fiber 24 within a circle 56 circumscribed by the minimum radius 52 is equal to the diameter of the circle 56. However, the spacing 58a between adjacent sections of the first side-emitting optical fiber 24 immediately outside of the circle 56 can be smaller than spacing 58b for straighter running sections of the first side-emitting optical fiber 24.

Sections leading to and leaving from the section of the first side-emitting optical fiber 24 that follows the minimum radius 52, which will be referred to as an inner-most looped section 24c, are also spaced from each other less than the minimum bend radius. This is accomplished because the inner-most looped section 24c bends around an angle Θ that is more than 180 degrees. More particularly, when the fabric panel 22 is laid flat (as shown in FIGS. 3 and 5), the first side-emitting optical fiber 24 bends more than 180 degrees back toward the optical fiber light sources 34, 36, 38, 40 housed in the electrical assembly 42. For the inner-most looped section 24c and the three looped sections 24d, 24e, 24f outside of and radially closest to the inner-most looped section 24c, these looped sections 24c, 24d, 24e, 24f bend back around at an angle that is greater than 270 degrees toward the electrical assembly 42 when the panel is laid flat. Also, each of these looped sections 24c, 24d, 24e, 24f follow a progressively larger respective radius that emanates from the same point. With reference back to FIG. 3, multiple looped sections similar to those shown in FIG. 5 are provided on the wrap 20. Again, such a lay out allows relatively large length of side-emitting optical fiber to be placed in relatively small area as compared to if the spacing was equal to the allowable bend radius.

Providing the inner-most looped section 24c (and adjacent looped sections) that bend around an angle Θ that is more than 180 degrees, however, results in the area inside the circle 56 being devoid of a light source. In view of this, the wrap 20 can include further light sources, which are distinct from the optical fiber light sources 34, 36, 38, 40 (FIG. 4) to which the side-emitting optical fibers 24, 26 are optically connectable. In the illustrated embodiment, these further light sources, which can be referred to as non-optical fiber light sources, can include LEDs 62, 64, 66, 68, 70, 72, 74, 76, which can be infrared ("IR") LEDs.

With reference to FIG. 3, each LED 62-76 is positioned on the fabric panel 22 within an area of the fabric panel 22 on which the side-emitting optical fibers 24, 26 are also provided. For example, as seen in FIG. 5, the LED 68 is shown having the side-emitting optical fiber 24 on opposite sides of the LED 68. More particularly, the LED 68 is positioned within the circle 56 to provide a further light source to an area that was once devoid of a light source. As seen in FIG. 3, each LED 62-76 can by bounded by a respective radius defining a respective looped section that follows the minimum radius 52. Although the section of the side-emitting optical fiber 24 that would close off the open part of the circle 56 is not visible in FIG. 5, as is more apparent with reference to FIG. 3, each LED 62-76 can be surrounded by a respective side-emitting optical fiber 24, 26.

The LED 68 depicted in FIG. 5 will be described with particularity with the understanding that the other LEDs, 62, 64, 66, 70, 72, 74, 76 can be similarly attached to the fabric panel 22. Each LED 62-76 is affixed to the inner surface 28 of the fabric panel 22. A sequin 78 can be affixed to the inner surface 28 of the fabric panel 22, and the LED 68 can be affixed to the inner surface 28 via the sequin 78. As such, the sequin 78 can be interposed between the LED 68 and the inner surface 28 of the fabric panel 22. An electrical wire 82 is connected with the LED 68 to deliver electrical power (and other signals, if desired) to the LED 68. The electrical wire 82 is retained against the inner surface 28 of the fabric panel 22. With reference back to FIG. 3, the electrical wire 82 can connect with a further electrical wire 84, or can be bundled with other electrical wires connected with the other LEDs, 62, 64, 66, 70, 72, 74, 76, and then pass through the second tunnel 44 in route to the electrical assembly 42.

Figure 4:
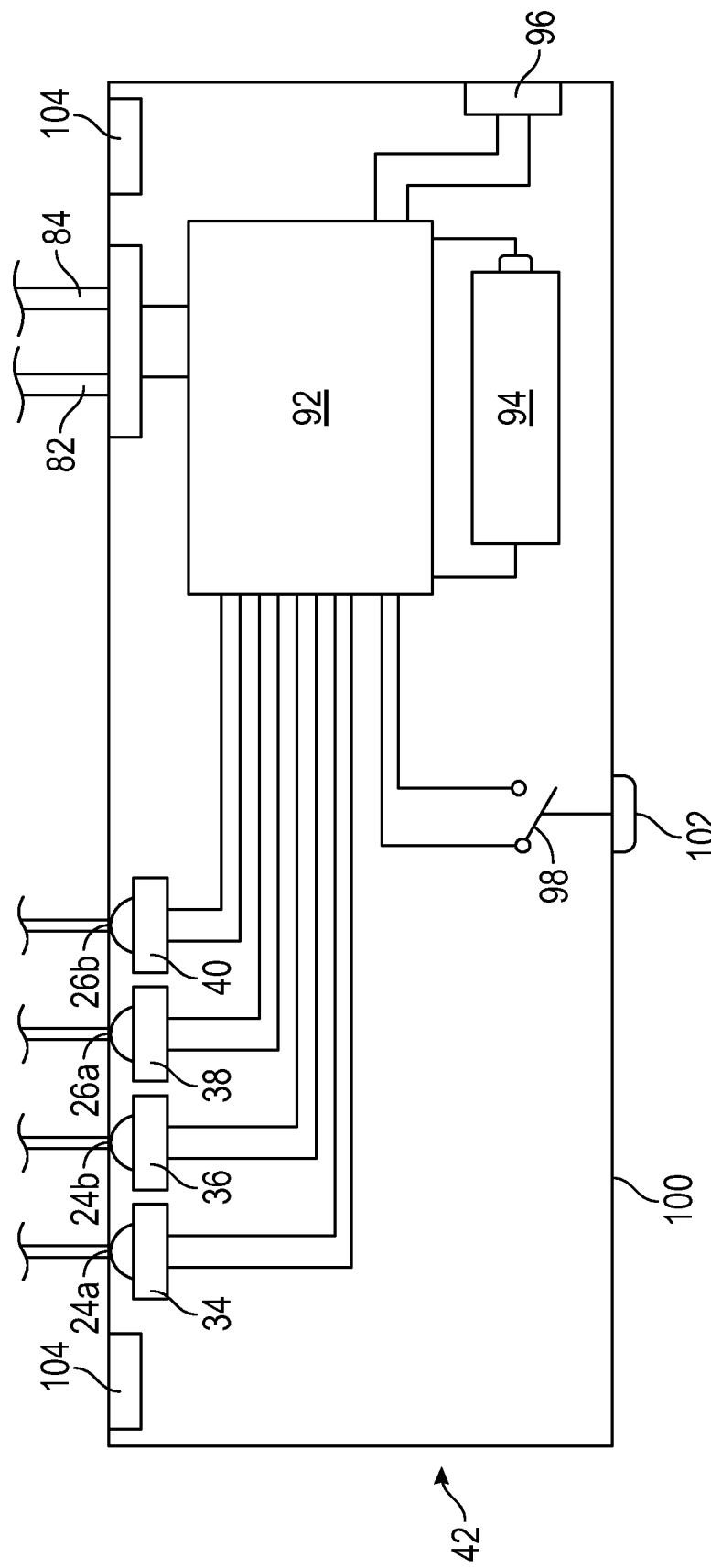
FIG. 4 is a schematic depiction of the electrical assembly for use with the wrap of FIG. 1 or another light therapy wearable.

FIG. 4 schematically depicts the electrical assembly 42. Each optical fiber light source 34, 36, 38, 40 can be an LED, a laser diode or another type of light source that emits light having a therapeutic wavelength. Thus, when optically connected with an appropriate light source emitting light having a therapeutic wavelength, each side-emitting optical fiber 24, 26 is configured to project light having a therapeutic wavelength toward a wearer of the wrap 20.

The electrical assembly 42 which can include a controller 92, e.g., an integrated circuit ("IC"), to which the electrical wires 82, 84 electrically connect. The controller 92 electrically connects with a power source, e.g., a battery 94, which can be rechargeable through a charging port 96. The controller 92 also electrically connects with a switch 98 that can control power delivery to the controller 92, thus controlling power to the LEDs 62, 64, 66, 68, 70, 72, 74, 76, and to the optical fiber light sources 34, 36, 38, 40 which are also electrically connected with the controller 92. The controller 92, the battery 94, and the switch 98 can be received in an electrical assembly housing 100, and an actuator 102, e.g., a button, can be accessible to a user on the outside of the electrical assembly housing 100 for operating the switch 98. The controller 92 can also be configured for wireless communication with an external device, e.g. a smartphone, via an application running on the external device. The controller 92 can also be configured to control the optical fiber light sources 34, 36, 38, 40 and the LEDs 62, 64, 66, 68, 70, 72, 74, 76 so as to control light being emitted in at least two different light-emitting zones. For example the controller 92 can operate in a mode where only the optical fiber light sources 34 and 36 are illuminated along with LEDs 62, 64, 66, 68, if desired, so as to illuminate only one zone of the wrap 20, while the optical fiber light sources 38, 40 and the LEDs 70, 72, 74, 76 are not illuminated. The electrical assembly 42 can be provided at any desirable location on the wrap 20, or it can be selectively attachable to the wrap 20 like what is shown in FIG. 2. For example, electrical assembly-side magnets 104 (FIG. 4) can cooperate with wearable-side magnets 106 (FIG. 2) to facilitate connection between the electrical assembly 42 and the wrap 20.

Figure 6:
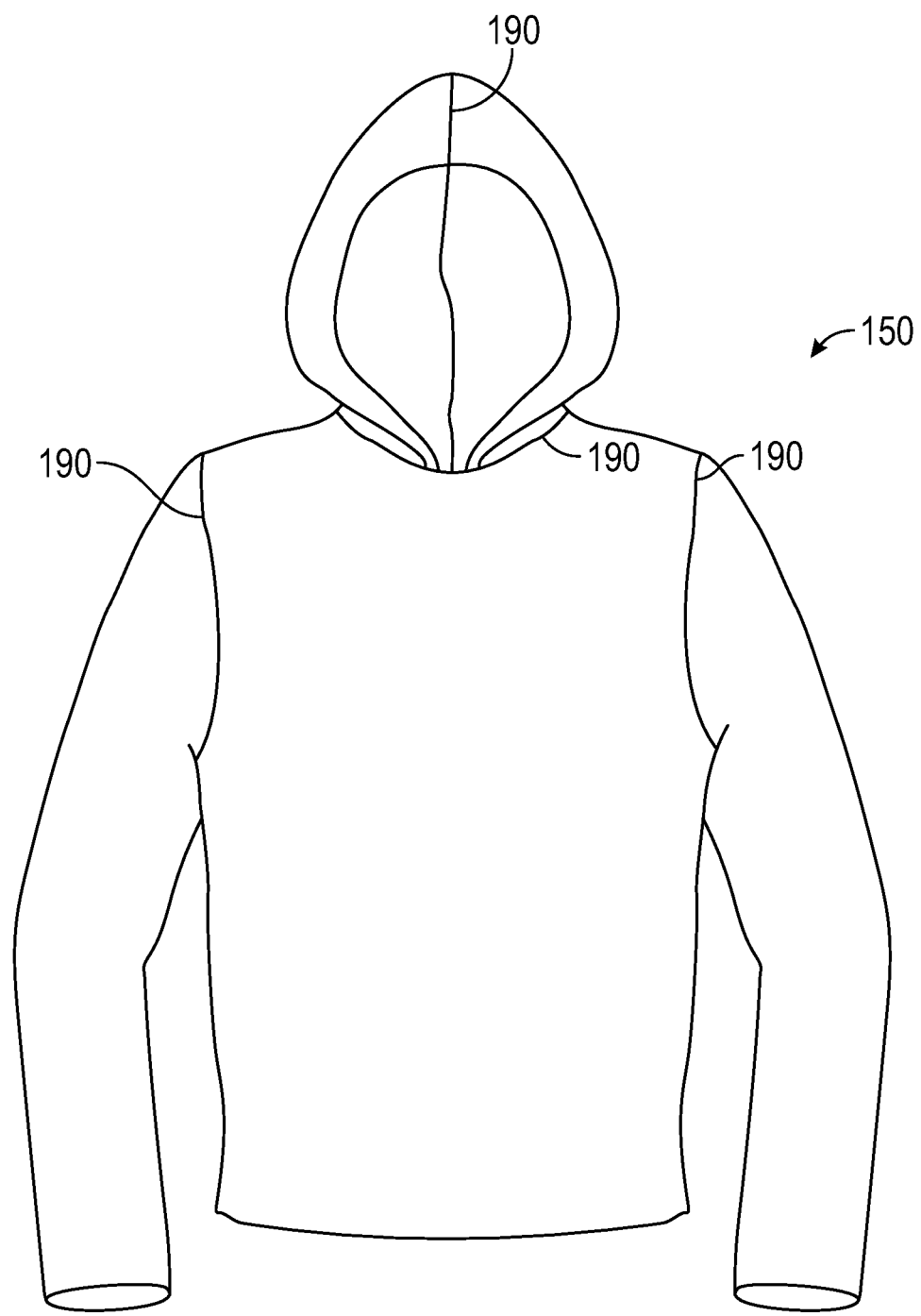
FIG. 6 is a front view of a light therapy wearable in the form of a garment for providing light therapy to a wearer of the garment.

FIG. 6 depicts a wearable in the form of a garment 150 for providing light therapy to a wearer. The garment 150 is manufactured in a manner so as to project light having a therapeutic wavelength, which has been described above, toward a person wearing the garment 150. The garment 150 can be configured to project light targeted body areas, which can include particular muscles, muscle groups, joints, human extremities, and the wearer's skin as examples. The garment 150 shown in FIG. 6 is a hoodie, however, the garment 150 can be another type of garment, such as a shirt, shorts, pants, gloves, a hat, socks, an undergarment, etc. The garment 150 is designed to be worn by a person in a similar manner as a conventional garment so that the hoodie shown in FIG. 6 would be worn over the upper body of a person.

Figure 7:
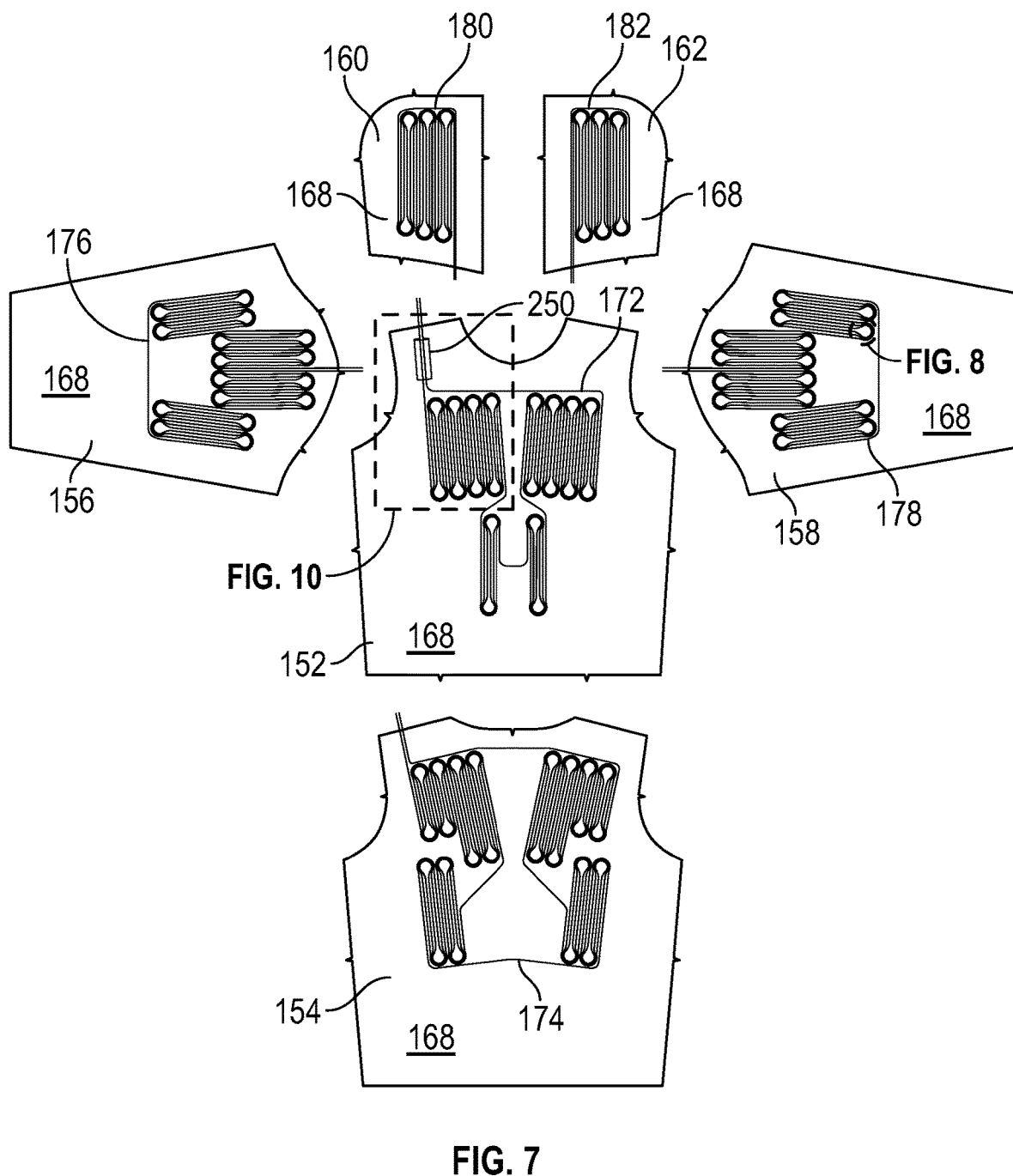
FIG. 7 is a plan view of panels laid flat and prior to being sewn together to make up the garment in FIG. 6.

With reference to FIG. 7, the therapeutic garment 150 is made up of a plurality of panels 152 (front), 154 (back), 156 (right sleeve), 158 (left sleeve), 160 (right hood), 162 (left hood) that when sewn together to make up the therapeutic garment 150. FIG. 6 depicts the panels 152-162 prior to being sewn together to form the garment 150 shown in FIG. 7. FIG. 7 is a plan view showing the inner surface 168 of each panel, which is the surface facing the wearer when the garment 150 is worn. The panels 152-162 can be either cut and sew pattern pieces or fully fashioned knitted structures. Where the panels 152-162 are cut and sew pattern pieces, each panel 152-162 is shown in FIG. 7 after being cut from standard fabric. Where the panels 152-162 are fully knitted structures, each panel in FIG. 7 is shown after manufacturing each knitted structure. When the plurality of panels 152-162 are sewn together, openings are provided for the head and arms for the garment 150 shown in FIG. 6. Openings can be provided for legs of the wearer where the garment takes another configuration, such as shorts, pants or underwear.

In either the cut and sew pattern pieces or fully fashioned knitted structures, the yarn from which each panel 152-162 is made can provide a comfort component for the garment 150. Examples of such yarn can include cotton, polyester, cotton/polyester blends, microdenier polyester/cotton blends, and combinations thereof. It can be desirable to provide the garment 150 so that it is skin-tight or form-fitting to bring the therapeutic light source, which will be described in more detail below, very close to the wearer of the garment 150. Accordingly, the yarn can also include an elastic fiber such as lycra or spandex, and more than one type of yarn can form each panel.

Each of the panels 152-162 can be made from fabric having a four way stretch, i.e., each panel can have 100% or nearly 100% recovery along the grain and cross grain from 8% stretch. This can be desirable when the garment 150 is a shirt. Each of the panels 152-162 can be made from fabric having 100% or nearly 100% recovery along the grain and cross grain from 30% stretch, which can be useful when the garment is a sock or wrap, for example. When the panels are cut and sew pattern pieces, each of the panels 152-162 can be either woven or knitted. When the panels are fully fashioned knitted structures, each of the panels 152-162 are a knitted structure typically made with little or no extra fabric.

FIG. 7 depicts side-emitting optical fibers 172, 174, 176, 178, 180, 182 affixed to the inner surface 168 of each panel 152, 154, 156, 158, 160, 162 respectively. Each side-emitting optical fiber 172-182 is optically connectable with a light source, which will be described in more detail below, and is configured to project light having a therapeutic wavelength toward a wearer of the garment 150. The side-emitting optical fibers 172, 174, 176, 178, 180, 182 can be the same as the side-emitting optical fiber 24, 26 described above with reference to the wrap 20. Unlike being woven or knitted into the panel similar to a typical yarn that makes up the panel, the side-emitting optical fiber 172-182 is affixed to the inner surface 168 of each panel 152-162 after the panel has been made, e.g., it is an additional step in the manufacturing process. By affixing each side-emitting optical fiber 172-182 to the inner surface 168 of each panel 152-162 after the panel has been made, more freedom as to the location and density of the side-emitting optical fiber is available in manufacturing the garment 150.

Figure 8:
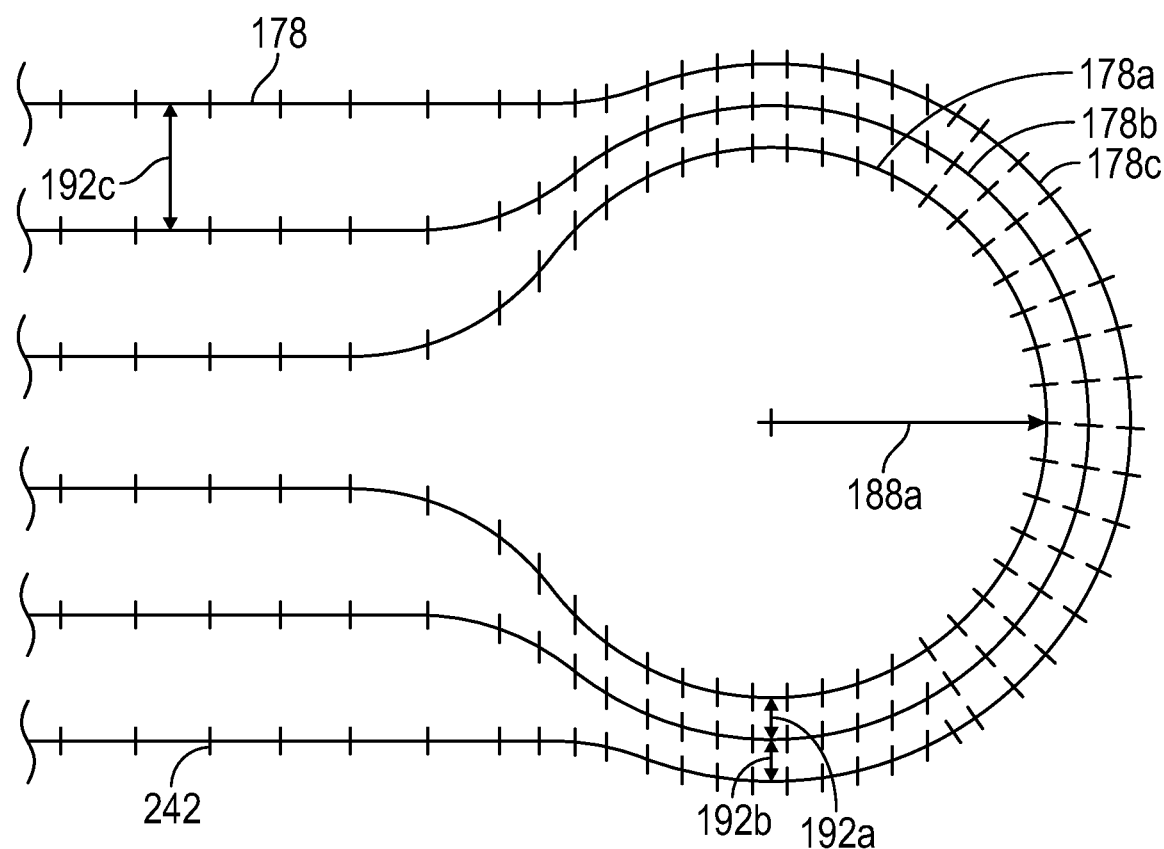
FIG. 8 is a close-up view of a portion of the garment shown in FIG. 7.

FIG. 8 depicts a close-up view of the panel 158 and the side-emitting optical fiber 178. Similar to the side-emitting optical fiber 24, 26 described above with reference to the wrap 20, the side-emitting optical fiber 178 is laid out having respective looped sections 178a, 178b, 178c, and a fewer or greater number of looped sections can be provided. Each looped section 178a, 178b, 178c has a radius (only a minimum radius 188a for looped section 178a is shown in FIG. 8 for purposes of clarity) that is greater than spacing 192a between respective looped sections 178a and 178b, greater than spacing 192b between respective looped sections 178b and 178c and spacing 192c between straighter adjacent sections of the side-emitting optical fiber 178 outside of the area bounded by the radius 188a of the innermost looped section.

Similar to the side-emitting optical fiber 24, 26 described above with reference to the wrap 20, the side-emitting optical fiber 172-182 has an allowable bend radius that is at least 36 times the outer diameter. To further mitigate against light loss, the minimum radius 188a can be at least 50 times the outer diameter of the side-emitting optical fiber. Spacing, which is measured perpendicular to the direction in which the side-emitting optical fiber 178 is running, between adjacent sections of the side-emitting optical fiber 178 along much of the side-emitting optical fiber 178 is less than the minimum radius 188a. Such a lay out allows relatively large length of side-emitting optical fiber to be placed in relatively small area as compared to if the spacing was equal to the allowable bend radius. The layout also allows for good light emission consistency along the length of the side-emitting optical fiber 178. The spacing between adjacent sections of the side-emitting optical fiber 178, however, need not be equal to one another. The spacing 192a, 192b, 192c between adjacent sections of the side-emitting optical fiber 178 can be smaller than the allowable bend radius by providing the respective looped sections 178a, 178b, 178c, which have a radius (e.g., the radius 188a for the innermost looped section 178a) that is greater than the allowable bend radius. Sections leading to and leaving from the innermost looped section 178a are also spaced from each other the spacing 192c less than the allowable bend radius.

Figure 9:
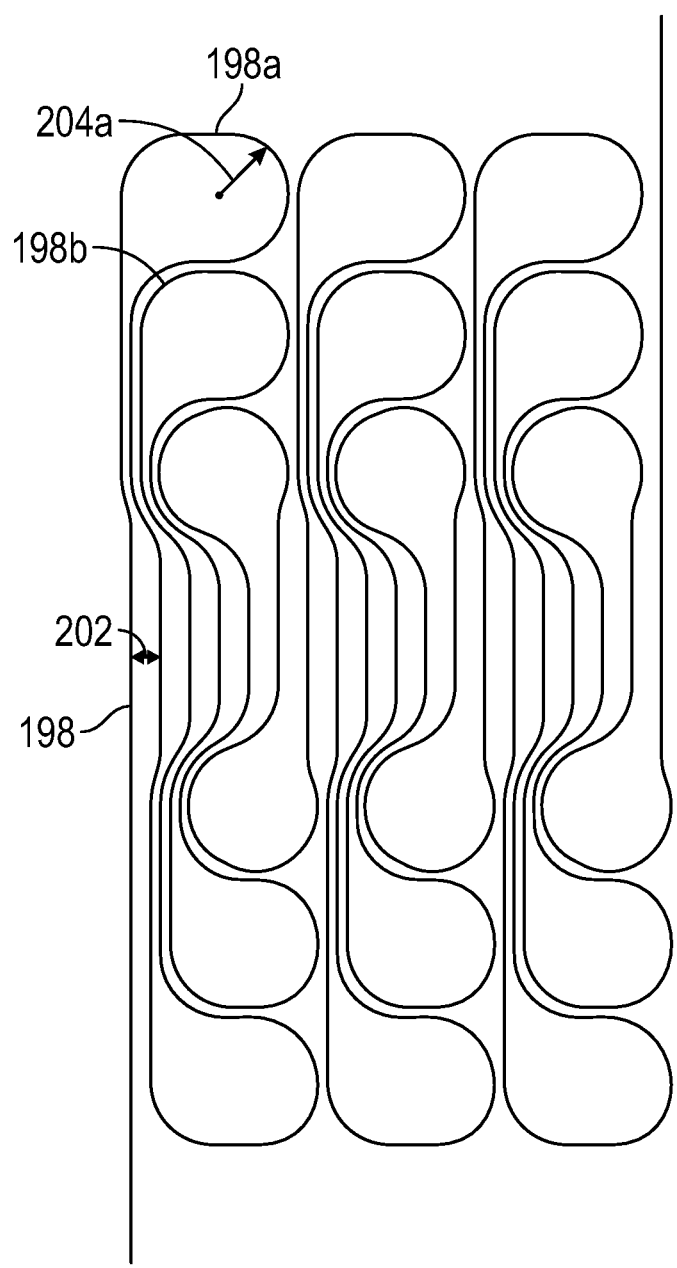
FIG. 9 is a plan view of a panel having an alternative side-emitting optical fiber layout.

FIG. 9 depicts an alternative side-emitting optical fiber 198 layout, which could be used in addition to or in lieu of the layout depicted in FIG. 3 for the wrap 20 and 7 for the garment. As in the layout depicted in FIG. 7, respective looped sections 198a, 198b, for example, are laid out with a radius (e.g., radius 104a) that is greater than the allowable bend radius of the side-emitting optical fiber 198, which can be the same as the side-emitting optical fiber 24, 26 described above. Spacing 202 between adjacent sections of the side-emitting optical fiber 198 outside of the area bounded by the radius of each looped section can be smaller than allowable bend radius. Also, the layout of the side-emitting optical fiber 24, 26 with the LEDs 62, 64, 66, 68, 70, 72, 74, 76 as additional light sources could be employed with the garment 150.

There are a number of ways to affix the side-emitting optical fibers to the respective panels. These ways will be described with reference to FIG. 8 with the understanding that the side-emitting optical fibers described throughout this specification can be affixed to the respective panel in a similar manner. For example, FIG. 8 depicts the side-emitting optical fiber 178 is via embroidery to the panel 158 (FIG. 7). Alternatively, the side-emitting optical fiber 178 can fixed via adhesive to the panel 158. In contrast to being affixed via adhesive, embroidery can allow for movement of the side-emitting optical fiber 178 along the length of the side-emitting optical fiber with respect to the panel 158 to which the side-emitting optical fiber is affixed. The side-emitting optical fiber 178 can also be pushed through the fabric that makes up the panel 158, e.g., the side-emitting optical fiber could be pushed through the panel so as to be visible on an outer surface (not visible in FIG. 8) of the panel. In this alternative where the side-emitting optical fibers are pushed through the fabric that makes up the panel, another outer layer of fabric may be provided over the outer surface of the panel.

Embroidery of the panel 158 in FIG. 8 will be described with particularity, with the understanding that the other panels including those for the wrap 20 can be similarly embroidered. When using embroidery to affix the side-emitting optical fiber 178 to the panel 158, a stitch spacing for embroidery stitches 242 can be non-uniform along the side-emitting optical fiber 178. The stitch spacing is the distance between embroidery stitches 242 traveling in the same direction. The smaller the stitch spacing, the closer the embroidery stitches 242 are to one another. For example, the stitch spacing along relatively tighter curved sections (sections having a relatively smaller radius) of the side-emitting optical fiber 178 is smaller than the stitch spacing along relatively straighter sections (sections having a relatively larger radius) of the side-emitting optical fiber 178. Providing more embroidery stitches 242 per unit length along the relatively tighter curved sections inhibits the side-emitting optical fiber 178 along the relatively tighter curved sections from lifting away from the panel 158 as the panel is bent and twisted while the garment 150 is being worn, for example.

The fiber used for embroidery, which makes up the embroidery stitches 242, can be a clear (transparent) or translucent fiber.

When using adhesive to affix the side-emitting optical fiber 178 to the panel 158, a continuous line of adhesive can be applied to the panel 158 and the side-emitting optical fiber 178 can be pressed against the adhesive until the adhesive cures. Alternatively, adhesive can be applied at discrete locations to the panel 158, e.g., drops of adhesive can be applied in each location where an embroidery stitch 242 is shown on the panel 158 in FIG. 8, and the side-emitting optical fiber 178 can be pressed against the adhesive until the adhesive cures. Also, fabric tape, which can be clear and includes an adhesive, can be used to affix the side-emitting optical fiber 178 to the panel 158.

Figure 10:
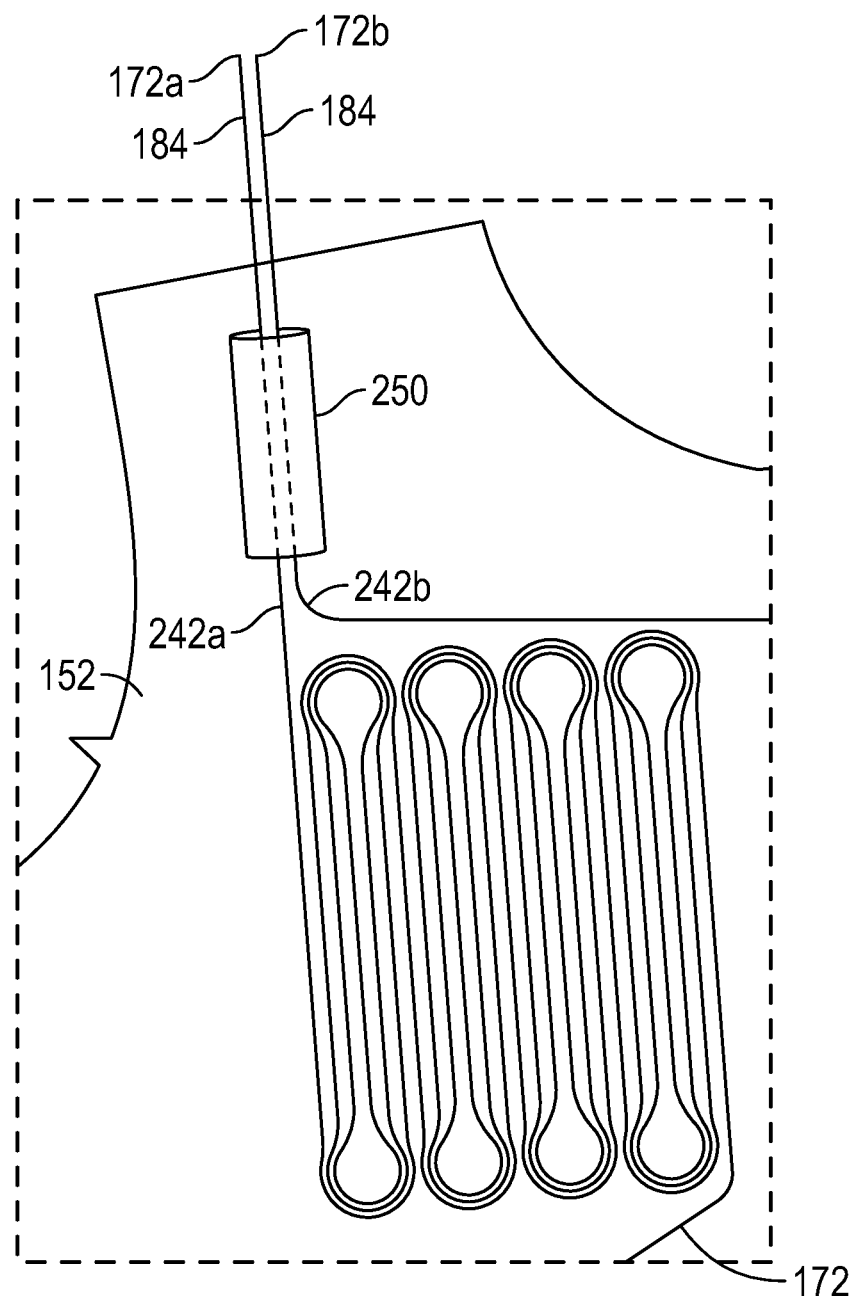
FIG. 10 is a close-up view of a portion of the garment shown in FIG. 7.

With reference back to FIG. 7, prior to sewing the panels 152-162 together to form the garment 150, each side-emitting optical fiber 172-182 includes at least two tails 184, which is a section of the respective side-emitting optical fiber between where the respective side-emitting optical fiber is affixed to the respective panel and a respective free end of the respective side-emitting optical fiber. Each tail 184 is movable away from the respective panel. For example, with reference to the portion of the panel 152 depicted in FIG. 10, each tail 184 is the section of the side-emitting optical fiber 172 that extends beyond the first embroidery stitch 142a and the last embroidery stitch 142b, which are the only two embroidery stitches shown in FIG. 10 for clarity purposes, to the respective free ends 172a, 172b. In the case of using an adhesive to attach the side-emitting optical fiber 172 to the panel 152, each tail 184 includes the section of the side-emitting optical fiber 172 that extends beyond the location where the side-emitting optical fiber 172 is first or last adhered to the panel 152, which would also typically be near a peripheral edge of the panel, to the respective free ends 172a, 172b.

Each tail 184 can also extend beyond a peripheral edge of the panel 152 to facilitate later routing of the side-emitting optical fiber 172 to the optical fiber light source, which will be described in more detail below. By providing two tails for each side-emitting optical fiber 172-182, both ends of each side-emitting optical fiber can receive light from the optical fiber light source. Providing light through both ends of each side-emitting optical fiber 172-182 can help with light attenuation as compared to if only one end of the side-emitting optical fiber was optically connected with the light source. By providing light through both ends of each side-emitting optical fiber, light attenuation calculations can be based on one-half the length of the side-emitting optical fiber.

As light travels along a length of optical fiber, some of it is absorbed or scattered. The sum of these absorption and scattering losses is referred to as attenuation. For side-emitting optical fiber, this attenuation can be used to determine what percentage of light remains in the optical fiber; for instance, if an optical fiber is lit from one side, it is possible to theoretically determine the amount of light remaining at any length using the following formula:

$$P(l) = P_0 10^{\frac{-a}{10}l}$$

where α is the average attenuation for the treatment wavelength (e.g., 0.4 dB/m at 650 nm), where P(l) refers to the optical power, which is measured in Watts, of light remaining in the optical fiber at length l, and $P_0$ refers to the optical power launched in the optical fiber. Additionally, it is possible to determine how much light remains at any length if an optical fiber if it is lit from both sides. The formula below can be written in different formats to help clarify the relationships between attenuation, length, consistency, and efficiency:

$$P(l) = P_0\left(10^{\frac{-\alpha}{10}l} + 10^{\frac{-\alpha}{10}(L-l)}\right)$$

where L is the total length of the optical fiber. To determine length based on efficiency, the following formula can be used:

$$L = -\frac{10*\log(1-\eta)}{\alpha}$$

Referring to the formulas above, the following points hold true. Using long lengths of optical fiber allows more light to escape out the sides of the optical fiber and towards the skin of the wearer of the wearable and a higher efficiency. This comes along, however, with more inconsistency along the optical fiber's length. Quantitatively, using an optical fiber length that allows for 90% of the light to escape out the sides will yield a theoretical minimum relative intensity of 0.575 or 57.5% of the maximum intensity at the middle of the length of optical fiber. Conversely, using short lengths of optical fiber allows for very consistent lighting from the sides of the optical fiber; however, this comes along with less light exiting the sides of the fiber and a lower efficiency. Quantitatively, using a fiber length that allows for 10% of the light to escape out the sides will yield a theoretical minimum relative intensity of 0.999 or 99.9% of the maximum intensity at the middle of the length of the optical fiber. As consistency does not seem to be too limiting, it makes sense to set an upper bound on usable optical fiber length as a function of attenuation. As such, when affixed to the fabric panel 22, each side-emitting optical fiber 24, 26 can have a length in meters no less than the quotient of 0.46 and the average attenuation of the side-emitting optical fiber 24, 26, as expressed by the following formula:

$$L > \frac{0.46}{\alpha}.$$

When using embroidery to affix the side-emitting optical fibers 172-182 to the respective panels 152-162, the embroidery stitches 242 allow for movement of the side-emitting optical fiber along the length of the side-emitting optical fiber with respect to respective panel. While allowing for movement of the side-emitting optical fiber along the length of the side-emitting optical fiber with respect to respective panel, the embroidery stitches 242 inhibit the side-emitting optical fibers from lifting away from the respective panels. Allowing for movement of the side-emitting optical fiber with respect to respective panel while inhibiting the side-emitting optical fibers from lifting away from the respective panels allows for the fabric that makes up the panels to have a greater elasticity than the side-emitting optical fiber. As mentioned above, the side-emitting optical fibers 172-182 have little or no elasticity, or at least much less than the respective panels 152-162. Each of the panels 152-162, however, can be made from fabric having a four way stretch, i.e., each panel can have 100% or nearly 100% recovery along the grain and cross grain from 8% stretch. Moreover, if desired, each of the panels 152-162 can be made from fabric having 100% or nearly 100% recovery along the grain and cross grain from 30% stretch. As such, the fabric that makes up each panel can provide for a skin-tight form-fitting garment 150 when the garment is finally assembled. Such a construction brings the side-emitting optical fibers 172-182 very close to the wearer's skin by providing a form-fitting garment can increase the therapeutic benefit of the garment 150.

Providing the tails 184 and affixing the side-emitting optical fibers 172-182 to the inner surface 168 of each panel 152-162 after each panel has been made and prior to sewing the panels together to form the garment 150, provides some advantages. With reference to FIG. 6, the plurality of panels 152-162 have been sewn together to provide seams 190 where the panels are joined. Since FIG. 6 shows the outside of the garment 150, the side-emitting optical fibers 172-182 are not visible (although they may be visible when emitting light). With reference to FIGS. 6 and 7, the side-emitting optical fibers 172-182 are provided on opposite sides of respective seams 190. By affixing the side-emitting optical fibers 172-182 to the inner surface 168 of each panel 152-162 after each panel has been made and prior to sewing the panels together, the side-emitting optical fibers can be provided on opposite sides of each seam, and then can be later connected to a light source.

A tunnel 250, which can be similar in all aspects to the tunnels 44, 46 described above with reference to FIG. 3, is shown provided on the panel 152. The tails 184 extending from the panel 152 can be routed through the tunnel 250 on the panel 152 in route to the optical fiber light source. FIGS. 7 and 9 show only one example of a location for the tunnel 250, and similar tunnels can be provided elsewhere on the garment 150. Alternatively, adhesive or adhesive tape can be provided to secure the tails 184 that are routed toward the optical fiber light source. For example, adhesive or adhesive tape can be provided on the panel 152 in the same or a similar location as the tunnel 250 to secure the tails 184 extending from the panel 152 when the garment 150 is finally assembled. The length of each tail 184 can be up to 250 cm (about 100 in) to accommodate different light source locations. A tail length of up to 250 cm is about equal to the diagonal distance between the outer left shoulder and the lower right corner of the (back) panel 154, which would allow for the light source to be located nearly anywhere on the panel 154.

Also, each side-emitting optical fiber 172-182 can follow a curvature of an anatomical structure of the wearer of the garment 150. For example, the panel 158 shown in FIG. 7 is a left sleeve of the garment 150 when the garment is finally assembled. The side-emitting optical fiber 178 is positioned on the panel 158 to project light onto the deltoid, bicep and triceps of the wearer of the garment 150. The side-emitting optical fiber 178 can follow a curvature, and where the panel 158 is made from an elastic fabric, the curvature of the side-emitting optical fiber 178 can change to conform to the wearer's left deltoid, bicep and triceps. This following the curvature of an anatomical structure of the wearer of the garment 150 can be accomplished for the other side-emitting optical fibers 172-182 as well. With the intensity of light being inversely proportional to the square of the distance from the light source, bringing the side-emitting optical fibers very close to the wearer's skin by conforming to an anatomical structure of the wearer of the garment 150 can increase the therapeutic benefit of the garment.

Figure 11:
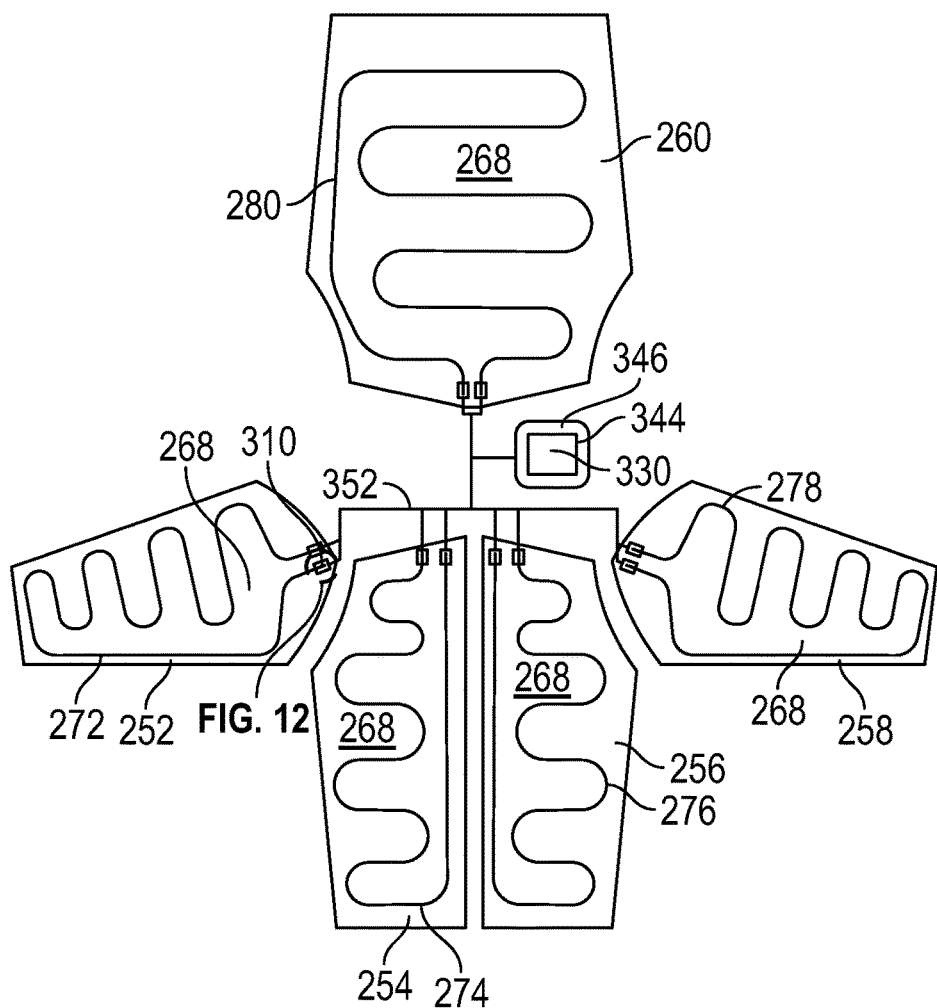
FIG. 11 is a plan view of panels laid flat prior to being sewn together to make up a garment depicting one manner of delivering light to a wearer of the garment.

FIG. 11 depicts panels 252, 254, 256, 258, 260 prior to being sewn or otherwise affixed together to form a garment (e.g., a shirt) where each panel is provided with a light source assembly 310 for each end of the respective side-emitting optical fiber 272, 274, 276, 278, 280 on the respective panel. The layout of the side-emitting optical fibers 272-280, which can be the same as the side-emitting optical fibers 172-182, is simplified in FIG. 11, however the side-emitting optical fibers 272-280 can be laid out on the respective panels similar to any of the above-described side-emitting optical fiber layouts. In FIG. 11, each panel 252, 254, 256, 258, 260 is provided with two light source assemblies 210.

Figure 12:
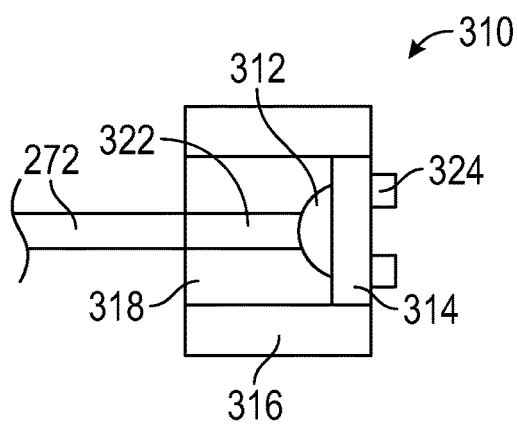
FIG. 12 is a schematic depiction of a light source assembly.

FIG. 12 is a schematic depiction of the light source assembly 310 in which an LED 312 is mounted to a circuit board 314, which are both received in a light assembly housing 316. Another type of light source, e.g., a laser diode, could be used instead of the LED. Also, the circuit board 314 need not be a rigid board, but could also be a flexible support with appropriate circuitry. Potting material 318, which can be clear or translucent, is provided over and around the LED 312, and can also surround terminal portions 222 of the respective side-emitting optical fiber 272-280 that receives light from the LED 312. Light source assembly side electrical contacts 324 extend from the circuit board 314 for receiving power.

Figure 13:
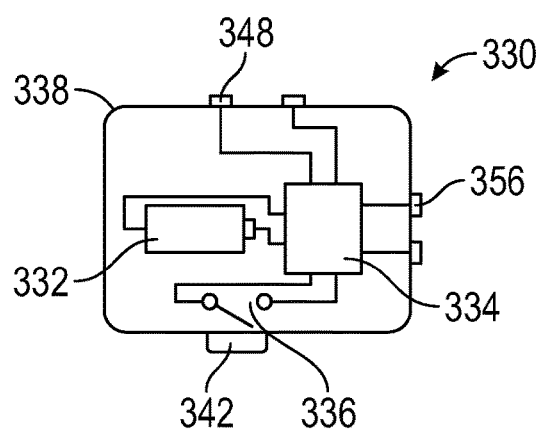
FIG. 13 is a schematic depiction of a power source assembly.

The light source assembly 310 cooperates with a power source assembly 330, which is schematically depicted in FIG. 13. The power source assembly 330 includes a battery 332 in electrical communication with a controller 334. The controller 334 can be an appropriate integrated circuit, for example. The controller 334 is in electrical communication with a switch 336 that can control power delivery to the light source assembly 310. The battery 332, the controller 334 and the switch 336 can be received in a power source housing 338, and an actuator 342, e.g., a button, can be accessible to a user on the outside of the power source housing 338 for operating the switch 336.

With reference bock to FIG. 11, the power source housing 338 is receivable in a power source recess 344 provided in a power source receptacle 346, which can be provided at any desirable location on the garment when the panels 252-260 are finally sewn or otherwise affixed together. When the power source assembly 330 is received in the power source receptacle 346, power supply contacts 348 are in electrical communication with the light source assembly side electrical contacts 324 via contacts (not visible) provided in the power source receptacle 346. With the power source assembly 330 in electrical communication with the light source assembly side electrical contacts 324 via wires 352, which can be appropriately routed along the finally assembled garment, and the switch 336 closed, power from the battery 332 can be supplied to the LED 312. Recharge contacts 356 can also be provided to recharge the battery 332 by connecting the recharge contacts 356 to another power source, e.g. a charger (not shown).

Figure 14:
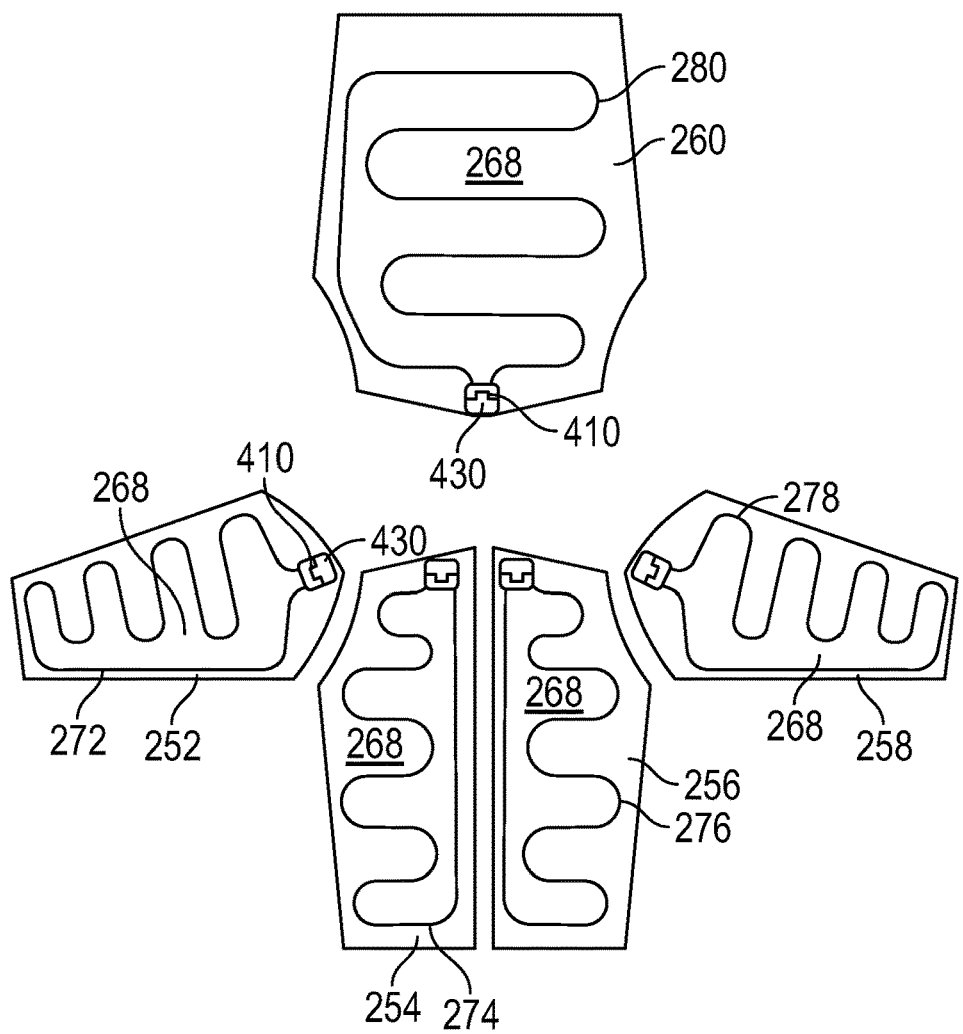
FIG. 14 is a plan view of panels laid flat prior to being sewn together to make up the garment depicting another manner of delivering light to a wearer of the garment.

FIG. 14 depicts panels 252-260 prior to being sewn or otherwise affixed together to form a garment (e.g., a shirt) where each panel is provided with a light source assembly 410 and a power source assembly 430 for each end of the respective side-emitting optical fiber 272-280 on the respective panel. Like FIG. 11, in FIG. 14 the layout of the side-emitting optical fibers 272-280 is simplified, however, the side-emitting optical fibers 272-280 can be laid out on the respective panels similar to any of the above-described side-emitting optical fiber layouts.

Figure 15:
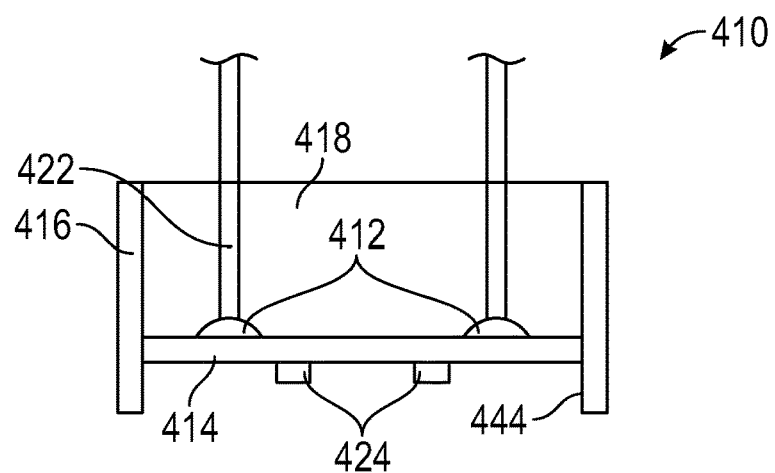
FIG. 15 is a schematic depiction of another example of a light source assembly.

FIG. 15 is a schematic depiction of the light source assembly 410 in which two LEDs 412, e.g. one for each end of the respective side-emitting optical fiber 272-280 on the respective panel, are mounted to a circuit board 414. The LEDs 412 and the circuit board 414 are both received in a light assembly housing 416. Potting material 418 is provided over and around the LEDs 412, and can also surround terminal portions 422 of the respective side-emitting optical fiber 272-280 that receives light from the LEDs 412. Light source assembly side electrical contacts 424 extend from the circuit board 414 for receiving power. Like in the embodiment shown in FIGS. 11-13, alternative light sources, such as laser diodes could be used instead of the LEDs 412. Additionally, the circuit board 414 need not be a rigid board, but could also be a flexible support with appropriate circuitry.

The light source assembly 410 cooperates with the power source assembly 430, which can be similar in all manners to the power source assembly 330 schematically depicted in FIG. 11 and thus will not be described in further detail. The power source housing 338 (FIG. 13) is receivable in a power source recess 444 provided in the light assembly housing 416, which can be provided at any desirable location on the respective panel 252-260. When the power source housing 338 is received in the power source recess 444, power supply contacts 348 (FIG. 13) are in electrical communication with the light source assembly side electrical contacts 424. With the power supply contacts 348 (FIG. 13) in electrical communication with the light source assembly side electrical contacts 424 and the switch 336 (FIG. 13) closed, power from the battery 332 can be supplied to the LEDs 412.

Figure 16:
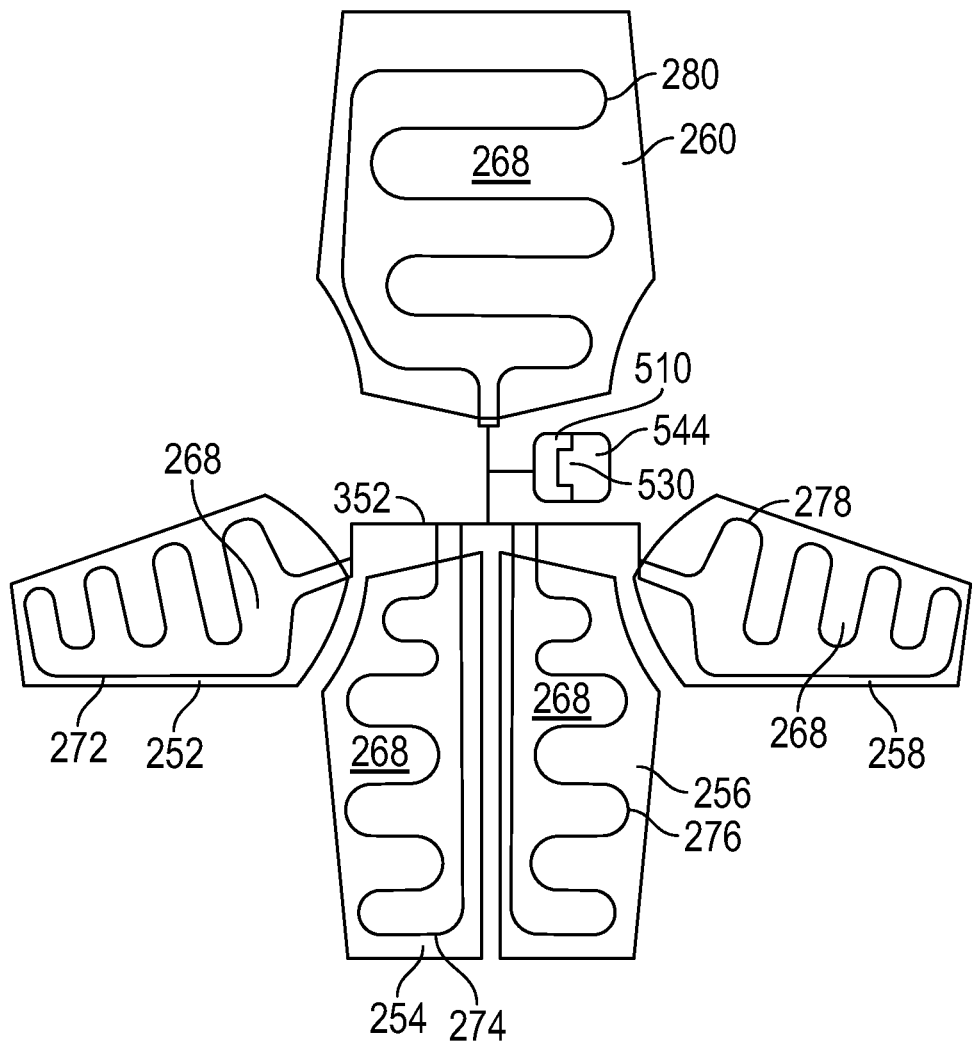
FIG. 16 is a plan view of panels laid flat prior to being sewn together to make up the garment depicting another manner of delivering light to a wearer of the garment.

FIG. 16 depicts panels 252-260 prior to being sewn or otherwise affixed together to form a garment (e.g., a shirt) where the side-emitting optical fibers 172-180 are bundled and optically connected with a light source assembly 510. The light source assembly 510 includes an LED (similar to the LED 312 depicted in FIG. 12) mounted to a circuit board (similar to the circuit board 214 depicted in FIG. 12), which are both received in a light assembly housing (similar to the light assembly housing 416 depicted in FIG. 15). As in the previously described embodiments, potting material can be provided over and around the LED, and can also surround terminal portions of the bundled side-emitting optical fibers 272-280. Light source assembly side electrical contacts (similar to the side electrical contacts 324, 424 depicted in FIGS. 12 and 15) extend from the circuit board for receiving power. The light source assembly 510 cooperates with the power source assembly 530, which can be similar in all manners to the power source assembly 330 schematically depicted in FIG. 13 and thus will not be described in further detail. The power source housing 338 (FIG. 13) is receivable in a power source recess 544 provided in the light assembly housing, which can be provided at any desirable location on the garment.

Figure 17:
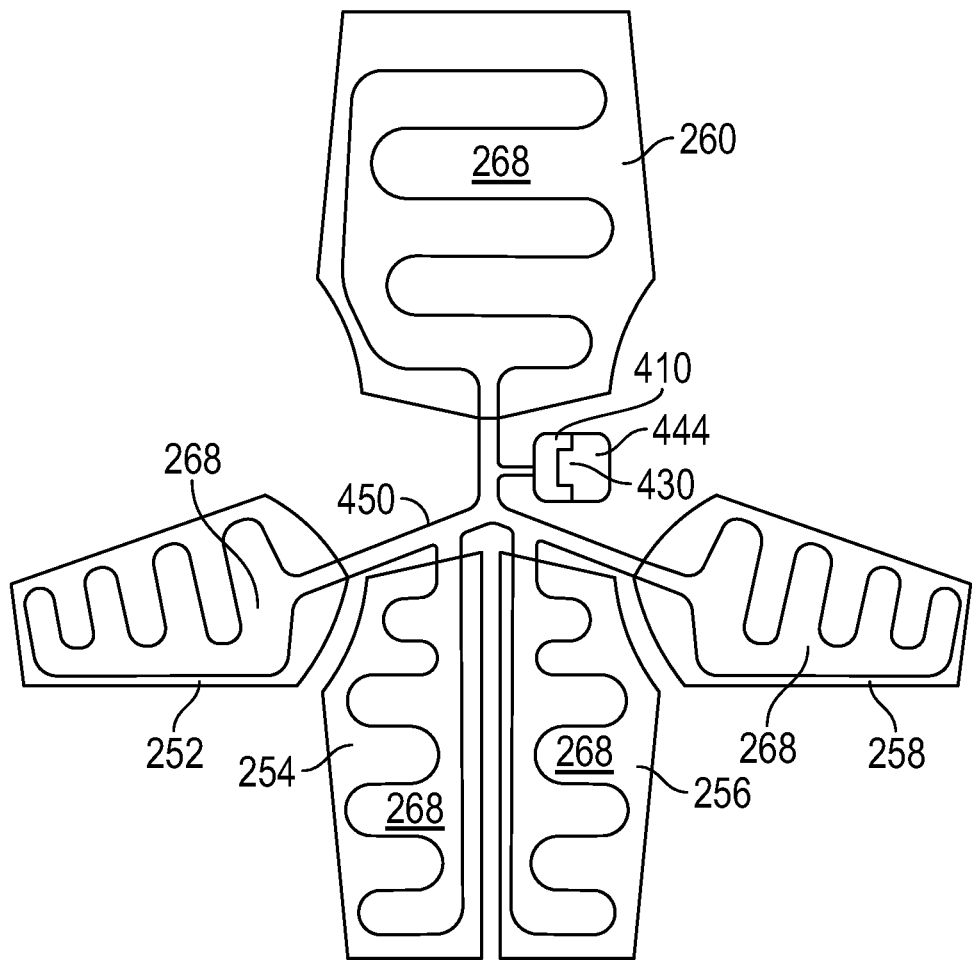
FIG. 17 is a plan view of panels prior to being sewn together to make up the garment depicting another manner of delivering light to a wearer of the garment.

FIG. 16 differs from FIG. 17 in that one side-emitting optical fiber 450, instead of a plurality of bundled side-emitting optical fibers, is optically connected with the light source assembly 410.

It will be appreciated that various of the above-disclosed embodiments and other features and functions, or alternatives or varieties thereof, may be desirably combined into many other different systems or applications. Also that various presently unforeseen or unanticipated alternatives, modifications, variations or improvements therein may be subsequently made by those skilled in the art which are also intended to be encompassed by the following claims.

The invention claimed is:

1. A wearable for providing light therapy to a wearer of the wearable, the wearable comprising:
   a plurality of fabric panels each having an inner surface that when the wearable is worn is configured to face a wearer's skin and an outer surface opposite the inner surface;
   an electrical assembly including a housing and at least one optical fiber light source configured to project light having a therapeutic wavelength provided in the housing, the housing being offset from the inner surface;
   a plurality of side-emitting optical fibers each affixed to the inner surface, each end of each of the plurality of side-emitting optical fibers being optically connectable with the at least one optical fiber light source and configured to project light having a therapeutic wavelength toward a wearer of the wearable,
   with the at least one fabric panel laid flat, each side-emitting optical fiber of the plurality of side-emitting optical fibers includes at least one looped section that bends around more than 180 degrees,
   sections of each side-emitting optical fiber of the plurality of side-emitting optical fibers of the wearable are bundled at a location on the inner surface adjacent where each side-emitting optical fiber transitions off of the inner surface prior to connecting with the at least one optical fiber light source, and the sections of each side-emitting optical fiber that are bundled are also spaced from each other on the inner surface in a direction parallel to the inner surface, wherein each side-emitting optical fiber of the plurality of side-emitting optical fibers has an allowable bend radius, which is a smallest radius that each side-emitting optical fiber can be bent before damage occurs to the side-emitting optical fiber that impacts its ability to transmit light along the length of the side-emitting optical fiber, and spacing, which is measured perpendicular to the direction in which the side-emitting optical fiber is running, between adjacent sections of each side-emitting optical fiber along at least a portion of each side-emitting optical fiber is less than the allowable radius.

2. The wearable of claim 1, wherein each side-emitting optical fiber of the plurality of side-emitting optical fibers includes a plurality of looped sections that each bend more than 180 degrees when the at least one fabric panel laid flat.

3. The wearable of claim 2, wherein the plurality of looped sections that each bend more than 180 degrees each follow a progressively larger respective radius emanating from the same point.

4. The wearable of claim 1, wherein one of the plurality of side-emitting optical fibers includes a plurality of looped sections that each bend around more than 180 degrees when the at least one fabric panel laid flat.

5. The wearable of claim 1, wherein each side-emitting optical fiber follows a minimum radius along the at least one looped section that is greater than or equal to the allowable bend radius.

6. The wearable of claim 5, wherein the minimum radius is at least 50 times an average outer diameter of each side-emitting optical fiber.

7. The wearable of claim 1, wherein each side-emitting optical fiber is embroidered to the at least one fabric panel.

8. The wearable of claim 7, wherein stitch spacing along relatively tighter curved sections of the each side-emitting optical fiber is smaller than the stitch spacing along relatively straighter sections of the each side-emitting optical fiber.

9. The wearable of claim 1, wherein each side-emitting optical fiber is adhered to the inner surface.

10. The wearable of claim 1, wherein at least one side-emitting optical fiber of the plurality of side-emitting optical fibers is pushed through the at least one fabric panel of the plurality of fabric panels so as to be visible on the outer surface of the at least one fabric panel.

11. The wearable of claim 1, wherein at least one fabric panel of the plurality of fabric panels has a greater elasticity than the at least one side-emitting optical fiber.

12. The wearable of claim 1, wherein the at least one fabric panel of the plurality of fabric panels includes a tunnel through which the at least one side-emitting optical fiber is routed.

13. The wearable of claim 12, wherein the tunnel receives first and second side-emitting optical fibers among the plurality of side-emitting optical fibers.

14. The wearable of claim 12, wherein the first and second side-emitting optical fibers each optically connect with a laser diode located in an electrical assembly.

15. A wearable for providing light therapy to a wearer of the wearable, the wearable comprising:
   a plurality of fabric panels each having an inner surface that when the wearable is worn is configured to face a wearer's skin and an outer surface opposite the inner surface; and
   a plurality of side-emitting optical fibers each affixed to the inner surface of at least one fabric panel of the plurality of fabric panels, each end of each of the plurality of side-emitting optical fibers being optically connectable with an the at least one optical fiber light source and configured to project light having a therapeutic wavelength toward a wearer of the wearable, wherein at least one side-emitting optical fiber of the plurality of side-emitting optical fibers is pushed through the at least one fabric panel of the plurality of fabric panels so as to be visible on the outer surface of the at least one fabric panel,
   with the at least one fabric panel laid flat, each side-emitting optical fiber of the plurality of side-emitting optical fibers includes at least one looped section that bends around more than 180 degrees, wherein each side-emitting optical fiber of the plurality of side-emitting optical fibers has an allowable bend radius, which is a smallest radius that each side-emitting optical fiber can be bent before damage occurs to the side-emitting optical fiber that impacts its ability to transmit light along the length of the side-emitting optical fiber, and spacing, which is measured perpendicular to the direction in which the side-emitting optical fiber is running, between adjacent sections of each side-emitting optical fiber along at least a portion of each side-emitting optical fiber is less than the allowable radius.

* * * * *